United States Patent [19]
Nagy et al.

[11] Patent Number: 5,753,208
[45] Date of Patent: May 19, 1998

[54] ANTIASTHMATIC AEROSOL PREPARATION OF SODIUM CROMOGLYCATE

[75] Inventors: Margit Nagy; Lidia Fedina; Rita Balazs; Borbala Barta, all of Budapest; Gizella Toth nee Gyarmati, Ullo; Judit Marczis; Andras Szasz, both of Budapest, all of Hungary

[73] Assignee: EGIS Gyogyszergyar, Budapest, Hungary

[21] Appl. No.: 61,356

[22] Filed: May 14, 1993

Related U.S. Application Data

[63] Continuation-in-part of Ser. No. 789,196, Nov. 8, 1991, abandoned.

[30] Foreign Application Priority Data

Nov. 9, 1990 [HU] Hungary .................... 7070/90

[51] Int. Cl.⁶ .................................................. A61K 9/12
[52] U.S. Cl. ........................................ 424/45; 424/43
[58] Field of Search ................................. 424/43, 45

[56] References Cited

U.S. PATENT DOCUMENTS

| | | | |
|---|---|---|---|
| 4,385,048 | 5/1983 | Mygind et al. | 424/45 |
| 4,405,598 | 9/1983 | Brown | 424/45 |
| 4,844,902 | 7/1989 | Grohe | 424/449 |
| 5,225,183 | 7/1993 | Purewal et al. | 424/45 |

FOREIGN PATENT DOCUMENTS 0993702  6/1965  United Kingdom.

Primary Examiner—Gollamudi S. Kishore
Attorney, Agent, or Firm—Beveridge, DeGrandi, Weilacher & Young LLP

[57] ABSTRACT

A pharmaceutical composition that is suitable for inhalation is disclosed, thus ensuring an effective treatment of the lungs. For this purpose, an aerosol composition is believed to be suited. The aerosol preparation comprises a stabilized suspension of sodium cromoglycate from which the active substance is favorably absorbed in the lungs after inhalation. In the aerosol preparation, 1 to 4% by mass of sodium cromoglycate is suspended in a mixture of propellants comprising 0.3 to 2.0% by mass of a dispersing agent consisting of oleyl oleate.

9 Claims, No Drawings

ANTIASTHMATIC AEROSOL PREPARATION OF SODIUM CROMOGLYCATE

REFERENCE TO RELATED APPLICATION

The present application is a continuation-in-part of our U.S. patent application Ser. No. 07/789,196 filed Nov. 8, 1991, now abandoned, which is incorporated by reference in its entirety.

BACKGROUND AND INTRODUCTION

The present invention relates to a new antiasthmatic aerosol preparation of solid disodium cromoglycate.

Sodium cromoglycate is known to have potent antiallergic activity including antiasthmatic activity. Sodium cromoglycate has been employed in the form of solid particles for the treatment of allergic conditions. A pharmaceutical microsphere formulation of sodium cromoglycate is described in U.S. Pat. No. 4,847,091 wherein the rate of release of the active substance is regulated by a material having ion-exchange properties.

In British Patent No. 993,702, aerosols are described which comprise:

(a) suspended solid agents, (b) a suspension medium consisting of propellants and esters prepared from $C_{8-18}$ carboxylic acids and $C_{3-8}$ alkanols, and (c) dispersing agents such as lecithin, lanolin, cholesterol and their derivatives. The dispersing agents are dissolved in the ester components of the suspension medium.

According to U.S. Pat. No. 4,241,048, benzocaine in finely powdered form is suspended in oils. During storage over a period of time, benzocaine changes its form becoming large, sharp needlelike crystals. In case of a preparation packaged in a pressurized aerosol container, this crystal growth produces a high incidence of valve clogging. The undesired crystal growth is prevented by incorporating an effective amount of a linear copolymer of a vinylpyrrolidone and a long chain alpha olefin.

Thus, from the state of art it is known that pharmaceutically active solid agents can be suspended in aerosol propellants; however, suitable dispersing agents are required to prevent the precipitation of the insoluble active agent from the dispersing medium and to meet a number of requirements. Thus, such dispersing agents:

have to be inert against the active ingredient and the dispersing medium; they should be biologically degradable, should not be toxic, should irritate contacting parts and organs of the body at the lowest degree possible, and should have appropriate odor and taste;

should provide an appropriate grade of dispersion in the dispersing medium and should confer suitable stability to the suspension; and should not inhibit but rather should enhance the dissolution of the active agent in the body fluids.

The appropriate choice of the type and amount of the dispersing agent(s) meeting the above requirements is a rather difficult task.

The prior art teaches first of all the use of the following dispersing agents in addition to the ones listed above:

oleyl alcohol, oleyl acid and esters thereof formed with polyvalent alcohols such as sorbitan monooleate /Span 80®/, sorbitan trioleate /Span 85®/, soya lecithin, etc. (Aerosol Age, August 1985; Canadian Patent No. 1,120,401).

SUMMARY OF THE INVENTION

It is an object of the present invention to provide a pharmaceutical composition that is suitable for inhalation, thus ensuring an effective treatment of the lungs. For this purpose, an aerosol composition is believed to be suited.

An object of the invention is to provide an aerosol preparation comprising a stabilized suspension of sodium cromoglycate from which the active substance is favorably absorbed in the lungs after inhalation.

The present invention discloses an aerosol preparation wherein 1 to 4% by mass of sodium cromoglycate is suspended in a mixture of propellants comprising 0.3 to 2.0% by mass of a dispersing agent consisting of oleyl oleate.

DETAILED DESCRIPTION OF THE INVENTION

In the present description and claims, an aerosol preparation of sodium cromoglycate means a suspension wherein solid disodium cromoglycate particles are suspended in a liquid; on releasing an aliquot of the suspension stored in a pressurized aerosol container, the liquid evaporates yielding an aerosol of sodium cromoglycate.

The sodium cromoglycate present in the aerosol preparation of the present invention may have a water content of as high as about 9% by mass without any deleterious effects. This is surprising because according to Canadian Patent No. 1,120,401 only an active agent with a water content of less than 5% by mass is appropriate for preparing aerosol compositions in suspended form of suitable quality.

The particle size of sodium cromoglycate being present in the aerosol composition of the present invention is important. In general, about 90% of the particles should be less than 10 µm, preferably less than 5 µm.

Sodium cromoglycate of the above particle size can be prepared by appropriate crystallization or any known method of pulverization.

The aerosol composition of the present invention may comprise any propellants which can be used in conventional aerosol products. The usual propellants are non-toxic compounds which are volatile at room temperature and atmospheric pressure, such as the following chlorofluoroalkanes: monofluorotrichloromethane (propellant gas 11), difluorodichloromethane (propellant gas 12) and tetrafluorodichloroethane (propellant gas 114), and others.

The aerosol composition of the present invention contains 0.3 to 2.0% by mass of a dispersing agent consisting of oleyl oleate. By definition, a dispersing agent is an agent added to a suspending medium to promote uniform and maximum separation of extremely fine solid particles, often of colloidal size. The usual dispersing agents are surface active agents as well (see Hawle's Condensed Chemical Dictionary (Van Nostrand Reinhold Company, New York, 11th edition, 1987, page 433) wherein "dispersing agents" are characterized to be surface active agents).

Surface active agents are characterized by a well defined HLB (hydrophilic/lipophilic balance) value. Oleyl oleate has no HLD value, thus it is not a surface active agent; however, it gives a higher stability for the suspension than the known dispersing agents of the prior art. Experimental data supporting this observation will be shown in a subsequent part of the description.

The aerosol composition of the present invention may contain, in addition to the constituents defined above, an additive consisting of 0.01 to 0.5% by mass of polyoxyethylene sorbitan monooleate and/or sorbitan trioleate.

The aerosol composition of the invention is prepared by known methods.

According to the so-called "cold filling", oleyl oleate and optionally additive(s) is/are dissolved in a mixture of the propellants cooled to about −50° C., then sodium cromoglycate is added, and the suspension obtained is filled into aerosol bottles that are closed using appropriate dosing valves. As propellants a mixture of propellant gas 11 having a boiling point of +24° C., propellant gas 12 having a boiling point of −30° C. and propellant gas 114 having a boiling point of +4° C. is preferred. The above mixture needs an efficient cooling to avoid evaporation of the most volatile ingredient (propellant gas 12).

According to the so-called "pressure filling", oleyl oleate and optionally the additive(s) is/are dissolved in the propellant having the highest boiling point (e.g., propellant gas 11), sodium cromoglycate is added, and the suspension is filled into aerosol bottles that are closed using appropriate dosing valves. Then the further gas constituent(s) having lower boiling point is/are filled under pressure into the bottles through the valves.

In practice, combinations of the above filling methods can be employed also.

At room temperature, the aerosol bottles filled according to any of the known methods contain three phases, i.e., solid particles of sodium cromoglycate, liquid propellant(s), and vapors of propellant(s). On releasing a dose of the suspension by pressing the valve, the liquid propellants evaporate yielding an aerosol of sodium cromoglycate. The latter aerosol is inhalated by the person to be treated, thus particles of sodium cromoglycate reach the lungs.

It was surprisingly found that oleyl oleate had very advantageous influences on both the stability of the suspension and the absorption of sodium cromoglycate in the lungs through the cell membrane. Without being bound by theory, it is believed that the small particles of sodium cromoglycate are covered by an oleyl oleate film and surprisingly the latter film influences the properties of the composition favorably both in a hydrophobic medium (in the suspension used) and in a hydrophilic medium (in the blood). In other words, the oleyl oleate film eliminates the agglomeration of the solid particles in the propellants and enhances the absorption of the solid particles after inhalation in the lungs.

The above statements are supported by the following experiments.

(A) The physical properties of the aerosol composition of the present invention were compared to those of known compositions of the prior art (Compositions II to IV) and of a control composition (Composition I). The preparation of Compositions I to IV is given after the Examples. The following parameters have been utilized in Table 1:

| | |
|---|---|
| volume of sediment in % by v/v; | VSE |
| Ability of the sediment for being redispersed (this property is given by the number of shakings necessary to redisperse the solids settled; shaking refers to a change of position of the bottle by 180°); | ABR |
| qualitative amount of sediment; | ASE |
| amount of solids adhering to the inner wall of the aerosol bottle in mg; | ASB |
| amount of solids adhering to the valve of the aerosol bottle in mg; | ASV |
| mean particle size in µm based on the number and volume of the solid particles, respectively (the determination was performed by a HIAC CP-420 type apparatus). | |

-continued

TABLE 1

Physical properties of aerosol compositions

| Example or Composition | VSE | ABR | ASE | ASV | ASB | Mean particle size based on number | Mean particle size based on volume |
|---|---|---|---|---|---|---|---|
| I | 2.9 | 30* | low | 22.3 | 9.50 | 3.20 | 9.41 |
| III | 2.6 | 25* | low | 23.6 | 7.70 | 3.38 | 9.77 |
| IV | 2.5 | 22* | low | 22.9 | 9.32 | 3.92 | 10.73 |
| 1 | 30 | 3 | high | 26.2 | 6.40 | 2.70 | 5.46 |
| 3A | 18.5 | 2 | medium | 16.2 | 6.20 | 3.13 | 5.74 |
| 5 | 35 | 2 | high | 23.5 | 7.20 | 3.33 | 7.40 |

*The compact sediment has been separated from the inner wall of the bottle but has not been redispersed in the liquid.

Table 1 indicates that in case of the known compositions of the prior art a very compact sediment forms that cannot be easily redispersed. Consequently, the value of VSE is low, ASE is characterized as "low" but ASE has a high value showing that a relatively large number of shakings are necessary to redisperse the settled solids.

In contrast, in the case of the compositions of the present invention, the volume and amount of the sediment are favorably high; thus only 2 to 3 shakings are necessary to redisperse the solids settled. In other words, the solid particles show a restricted agglomeration in the presence of oleyl oleate.

(B) The absorption of the inhalated active agent in the blood was determined in vitro using a Mühlemann type of dialysis apparatus shown in FIG. 1. The explanation of the symbols used in FIG. 1 is as follows:

1 sample addition
2 glass tube
3 receptor phase (phosphate buffer, pH=7.4)
4 from the thermostat
5 double-wall vessel for dialysis
6 to the thermostat
7 dialyse-membrane
8 magnetic stirrer
9 magnetic stirrer equipment (IKAMAG RCT).

A so-called membrane for renal dialysis (from HOECHST, Germany) was used as the membrane. The membrane was pretreated for 17 to 18 hours in a phosphate buffer having a pH value of 7.4 prior to the measurements.

50 ml of buffer solution were filled into the apparatus for the measurement. The temperature of the measuring system was held at 37° C., the stirrer was operated at 100 revolutions/minute.

Each of the different aerosol compositions tested were investigated using 3 parallel "doses" contacted with the membrane. One "dose" corresponds to the amount of composition released from the bottle by operating the dosing valve once after shaking the bottle; it contains about 1 mg of sodium chromoglycate. The amount of the active agent was determined by precisely weighing the bottle before and after releasing a dose, using an analytical balance.

After predetermined periods of time, specimens were taken from the receptor phase of the system and the amount of sodium chromoglycate transported from the donor phase was measured using a spectrophotometer.

The results of the analytical measurements are given in Table 2.

TABLE 2

Change of concentration of the active agent in the buffer solution in % by mass against time

| Example No. | Time, hours | | | | | |
|---|---|---|---|---|---|---|
| | 1 | 2 | 3 | 4 | 5 | 6 |
| I | 22.6 ± 2 | 36.6 ± 3 | 48.3 ± 6 | 54.7 ± 5 | 58.1 ± 7 | 60.9 ± 6 |
| II | 15.4 ± 2 | 27.1 ± 2 | 36.3 ± 2 | 42.9 ± 4 | 46.9 ± 5 | 48.8 ± 6 |
| III | 3.5 ± 1.5 | 10.2 ± 1 | 46.8 ± 2 | 58.3 ± 4 | 61.9 ± 6 | 64.0 ± 6 |
| IV | 5.6 ± 1.5 | 10.8 ± 1 | 42.3 ± 2 | 46.8 ± 2 | 47.8 ± 5 | 48.5 ± 6 |
| 5 | 44.9 ± 2 | 57.2 ± 2 | 58.1 ± 4 | 59.1 ± 4 | 59.9 ± 5 | 61.6 ± 5 |
| 1 | 51.6 ± 2 | 62.9 ± 3 | 70.1 ± 4 | 73.3 ± 3 | 74.3 ± 6 | 74.7 ± 6 |
| 3A | 32.0 ± 2 | 50.2 ± 3 | 56.4 ± 4 | 58.7 ± 35 | 60.9 ± 5 | 62.8 ± 5 |

From Table 2 it can be seen that in the test simulating the inhalation and absorption of the active agent sodium chromoglycate is absorbed at a substantially higher rate in the presence of oleyl oleate (Examples 1, 3A and 5) than in the absence of oleyl oleate (Compositions I to IV). Thus, in case of Example 1, after 1 hour the concentration of the active agent is already 51.6% and after 6 hours the concentration of the active agent is as high as 74.7%.

In contrast, in case of Composition I, the lower concentration value of Example 1 is reached after about 3.5 hours and after 6 hours 60.9% can be reached.

(C) The tests of item (B) were repeated using some aerosol compositions of the prior art and a composition of the present invention. The following compositions were used:

Composition "A"

Composition "A" corresponds to British Patent No. 993,702 wherein the isopropyl miristate was used as solvent for the dispersing agent sorbitan trioleate (Span 85). The sorbitan trioleate can be readily introduced into the system without any solvent or dispersing agent, so the solvent was used only in order to provide a model composition being identical with the present invention with the exception of dispersing agent; it is not necessary to separately dissolve or disperse it in a dispersing agent (such as lecithin, lanolin, cholesterol, etc.) as mentioned in the British Patent. Thus, composition "A" consists of the following components:

| Disodium chromoglycate | 0.300 g/bottle |
|---|---|
| Sorbitan trioleate | 0.010 g/bottle |
| Isopropyl miristate | 0.115 g/bottle |
| Propellant gas 11 | 11.875 g/bottle |
| Propellant gas 12/114 (50:50) | 5.000 g/bottle |

Composition "B"

In the case of this composition, isopropyl miristate was introduced into the system instead of oleyl oleate in the same amount. The components are as follows:

| Disodium chromoglycate | 0.300 g/bottle |
|---|---|
| Isopropyl miristate | 0.115 g/bottle |
| Propellant gas 11 | 11.885 g/bottle |
| Propellant gas 12/114 (50:50) | 5.000 g/bottle |

Composition "C"

This is a composition according to the present invention with the following ingredients:

| Disodium chromoglycate | 0.300 g/bottle |
|---|---|
| Sorbitan trioleate | 0.010 g/bottle |
| Oleyl oleate | 0.115 g/bottle |
| Propellant gas 11 | 11.875 g/bottle |
| Propellant gas 12/114 (50:50) | 5.000 g/bottle |

The membrane diffusion of sodium chromoglycate was investigated as given above under item (B). The results are summarized in Table 3.

TABLE 3

| Time in hours | Diffused active agent in % in case of composition | | |
|---|---|---|---|
| | A | B | C |
| 1 | 7.95 | 21.83 | 31.22 |
| 2 | 8.53 | 22.75 | 43.88 |
| 3 | 13.50 | 20.90 | 56.31 |
| 4 | 14.80 | 18.13 | 60.13 |
| 5 | 15.97 | 13.41 | 65.15 |
| 6 | 9.14 | 8.22 | 67.50 |

From Table 3 it can be seen that the amount of the diffused sodium chromoglycate active agent from the composition of the present invention is significantly higher than from those disclosed in the state of art.

If the concentration of the diffused active agent is plotted against time it is even more evident that in case of composition "C" according to the present invention, the membrane diffusion rises abruptly in the first 3 hours then the diffusion remains between 56% and 67% for the next 3 hours. At the same time, in case of the known compositions, the concentration attained with the composition of the present invention in the first hour cannot be attained even in 6 hours by the compositions "A" and "B".

The invention is further illustrated by the following non-limiting Examples.

Example 1

| Composition | % by mass |
|---|---|
| Disodium chromoglycate (having a water content of 9% by mass) | 1.7 |
| Oleyl oleate | 1.3 |
| Monofluorotrichloromethane | 70.7 |

-continued

Example 1

| Composition | % by mass |
|---|---|
| Difluorodichloromethane | 13.15 |
| Tetrafluorodichloroethane | 13.15 |
| | 100.00 |

The monoflurotrichloromethane is cooled to a temperature of 10° C. Oleyl oleate is dissolved in the cooled monofluorotrichloromethane and small portions of disodium chromoglycate are added to the mixture under continuous stirring (at amount 1400 revolutions/minute). The mixture is stirred during a period of 45 minutes (at about 2800 revolutions/minute). The suspension obtained is filled into aerosol bottles under continuous stirring (at about 1400 revolutions/minute) and cooling. The bottles are closed using appropriate dosing valves, then both of the further gas components, either mixed or separately, are filled under pressure into the bottles via the valve.

Example 2

| Composition | % by mass |
|---|---|
| Disodium chromoglycate (having a water content of 9% by mass) | 3.3 |
| Oleyl oleate | 0.6 |
| Polyoxyethylene sorbitan monooleate | |
| Monofluorotrichloromethane | 67.0 |
| Difluorodichloromethane | 14.5 |
| Tetrafluorodichloroethane | 14.5 |
| | 100.00 |

The monofluorotrichloromethane is cooled to a temperature of 5° C. Oleyl oleate and then polyoxyethylene sorbitan monooleate are dissolved in the cooled monofluorotrichloromethane. The solution obtained is added to the mixture of difluorodichloromethane and tetrafluoro dichloroethane cooled to −45° C. At this temperature the disodium chromoglycate is added in portions to the mixture under steady stirring (at about 2500 revolutions/minute). After a subsequent stirring period of 20 to 30 minutes, the suspension is filled into aerosol bottles under continuous stirring and cooling, and the bottles are closed using appropriate dosing valves.

Example 3

| | Composition containing a dose of | |
|---|---|---|
| | 1 mg (Example 3A) | 5 mg (Example 3B) |
| Composition | % by mass | |
| Disodium chromoglycate | 1.7 | 3.3 |
| Oleyl oleate | 0.66 | 0.53 |
| Sorbitan trioleate | 0.05 | 0.05 |
| Monofluorotrichloromethane | 68.64 | 69.82 |
| Difluorodichloromethane | 14.475 | 13.15 |
| Tetrafluorodichloroethane | 14.475 | 13.15 |
| | | 100.00 |

The composition is prepared as described in Example 1 with the difference that the sorbitan trioleate is dissolved after dissolution of the oleyl oleate. In a clinical test it was found that a dose of 1 mg of the composition obtained had the same effect as a capsule with the usual dose of 20 mg of disodium chromoglycate.

Example 4

| Composition | % by mass |
|---|---|
| Sodium chromoglycate | 1.7 |
| Oleyl oleate | 0.66 |
| Monofluorotrichloromethane | 69.74 |
| Difluorodichloromethane | 14.45 |
| Tetrafluorodichloroethane | 14.45 |
| | 100.00 |

The composition is prepared as described in Example 1.
Compositions I to IV

Compositions according to the prior art (Compositions II to IV) and a comparative composition (Composition I) were prepared in accordance with the process described in Example 1 with the difference that the sorbitan trioleate was dissolved in the cooled monofluorotrichloromethane, instead of oleyl oleate. The amounts of the components are given in Table 4.

TABLE 4

| | Amount in % by Mass | | | |
|---|---|---|---|---|
| Ingredients | I | II | III | IV |
| Disodium chromoglycate | 1.7 | 1.7 | 1.7 | 1.7 |
| Sorbitan trioleate | — | 0.1 | 0.5 | 1.5 |
| Monofluorotrichloromethane | 70.0 | 69.9 | 69.5 | 68.5 |
| Difluorodichloromethane | 14.15 | 14.15 | 14.15 | 14.15 |
| Tetrafluorodichloroethane | 14.15 | 14.15 | 14.15 | 14.15 |

What is claimed:

1. An aerosol preparation comprising 1 to 4% by mass of sodium cromoglycate suspended in a mixture of propellants containing 0.3 to 2.0% by mass of a dispersing agent consisting of oleyl oleate.

2. The aerosol preparation according to claim 1, further comprising 0.01 to 0.5% by mass of polyoxyethylene sorbitan monooleate and/or sorbitan trioleate.

3. The aerosol preparation according to claim 1, wherein the particle size of 90% of said sodium cromoglycate is less than 10 µm.

4. The aerosol preparation according to claim 3, wherein the particle size of 90% of said sodium cromoglycate is less than 5 µm.

5. The aerosol preparation according to claim 1, consisting essentially of 1 to 4% by mass of sodium cromoglycate suspended in a mixture of propellants containing 0.3 to 2.0% by mass of a dispersing agent consisting of oleyl oleate and optionally 0.01 to 0.5% by mass of polyoxyethylene sorbitan monooleate and/or sorbitan trioleate.

6. The aerosol preparation according to claim 1, consisting of 1 to 4% by mass of sodium cromoglycate suspended in a mixture of propellants containing 0.3 to 2.0% by mass of a dispersing agent consisting of oleyl oleate and optionally 0.01 to 0.5% by mass of polyoxyethylene sorbitan monooleate and/or sorbitan trioleate.

7. The aerosol preparation according to claim 1, wherein said mixture of propellants contains monofluorotrichloromethane, difluorodichloromethane, and tetrafluorodichloroethane.

8. The aerosol preparation according to claim 5, wherein said mixture of propellants contains monofluorotrichloromethane, difluorodichloromethane, and tetrafluorodichloroethane.

9. The aerosol preparation according to claim 6, wherein said mixture of propellants contains monofluorotrichloromethane, difluorodichloromethane, and tetrafluorodichloroethane.

* * * * *